United States Patent [19]

Shuster et al.

[11] 3,978,215

[45] Aug. 31, 1976

[54] LOCAL ANAESTHETIC

[76] Inventors: Yan Shuster, ulitsa Kveles 15, korpus 4, kv. 30, Riga; Valdis Danielovich Mikazhan, Stopinsky selsovet Tuber kuleznaya bolnitsa, Rizhsky raion; Milda Yanovna Pormale, ulitsa Suvorova, 104, kv. 10, Riga; Nadezhada Alexandrovna Kashkina, ulitsa Talsu, 9/11, kv. 22, Riga; Arvid Yanovich Kalninsh, ulitsa Sverdlova, 8, kv. 3, Riga, all of U.S.S.R.

[22] Filed: Jan. 6, 1975

[21] Appl. No.: 538,851

Related U.S. Application Data

[63] Continuation of Ser. No. 453,668, March 20, 1974, abandoned.

[52] U.S. Cl. .............................................. 424/180
[51] Int. Cl.² ........................................ A61K 31/70
[58] Field of Search ................. 424/180; 260/231 A

*Primary Examiner*—Jerome D. Goldberg
*Attorney, Agent, or Firm*—Haseltine, Lake & Waters

[57] ABSTRACT

A local anaesthetic which comprises as active ingredient a high-molecular weight derivative of the hydrochloride of the 2-diethylaminoethyl ester of p-aminobenzoic acid of the following general formula:

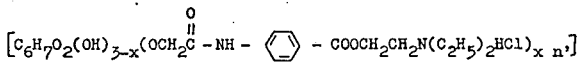

where $x$ is the degree of substitution from 0.6 to 1.0 and $n$ is the degree of polymerization from 40 to 120 — combined with a pharmaceutical solvent or an ointment base.

6 Claims, No Drawings

LOCAL ANAESTHETIC

This application is a Continuation Application of Ser. No. 453,668, filed Mar. 20, 1974, now abandoned.

The present invention relates to a novel local anaesthetic.

The local anaesthetic in accordance with the invention comprises as the active ingredient a high-molecular weight derivative of the hydrochloride of the 2-diethylaminoethyl ester of p-aminobenzoic acid of the following general formula:

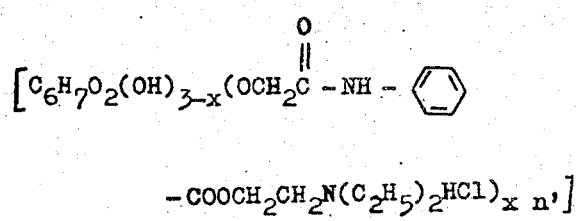

where $x$ is the degree of substitution from 0.60 to 1.00 and $n$ is the degree of polymerization from 40 to 120 — combined with a pharmaceutical solvent or an ointment base.

The active ingredient of the proposed preparation is an amorphous, hygroscopic, white substance, readily soluble in water and insoluble in organic solvents.

As to its action, the proposed preparation is not different from novocaine; it belongs to esters of p-aminobenzoic acid. As compared with novocaine, the proposed preparation is more active and its effect is more lasting. The local anaesthetic effects of the proposed preparation and novocaine were comparatively evaluated by using the Bulbring and Wajda technique on guinea pigs by intracutaneous administration of the active ingredient-containing solutions of nine different concentrations, from 0.015 to 3.66 mmoles/1, each dose being equal to 0.25 ml. The anaesthesia was regarded as complete when all 6 touches with an injection needle failed to cause skin twitching (6 units). A state when in two successive trials carried out at a five-minute interval all the 6 touches caused skin twitching (0 units) — was regarded as one of completely recovered sensitivity. The period of time from the instant of intracutaneous injection to the complete recovery of sensitivity characterized the duration of anaesthesia.

As follows from the results of the trials, as the high-molecular weight derivative of the hydrochloride of the 2-diethylaminoethyl ester of p-aminobenzoic acid increases in concentration, so does its deposition effect.

For a more accurate activity evaluation according to Miller and Tainter, the mean concentrations ($EC_{50}$) of the proposed preparation ensuring 50 percent anaesthesia within 30 minutes after injection were determined as well as its relative activity vis-a-vis novocaine. The results suggest that the proposed preparation is 4.8 times as potent as novocaine in terms of infiltration anaesthesia. By the duration of infiltration anaesthesia, the proposed preparation is 1.5 to 2 times as potent as the corresponding equimolar novocaine solutions.

Comparison of the concentrations providing for complete anaesthesia within 30 minutes after injection bears out the superiority of the proposed preparation to novocaine: under such conditions, novocaine ensures complete anaesthesia at a concentration of 3.66 mmoles/1, whereas the proposed preparation ensures this degree of anaesthesia already at a concentration of 0.46 mmole/1, i.e. at one-eighth the novocaine concentration.

The comparative data on the potency and duration of terminal (surface) anaesthesia were obtained on guinea pigs by the Bulbring and Wajda technique, whereby 1 drop of a solution of the proposed preparation and 1 drop of a novocaine solution were dripped into the conjunctival cul-de-sac of an animal. From the Renier index values thus obtained the mean was determined with the confidence limits for each concentration tested at $P = 0.05$. Besides, the cornea anaesthesia duration was taken into account by determining the Renier index every 5 minutes until corneal sensitivity had been fully restored, i.e. until the moment when touching the cornea with a hair immediately evoked the blinking reflex.

Comparison of the $EC_{50}$ values calculated by the Miller and Teinter method indicates that, in terms of terminal anaesthesia, the proposed preparation is 2.1 times as potent as novocaine.

By the duration of terminal anaesthesia, the proposed preparation in equimolar concentrations (by the level of the active ingredient) is 1.5 to 2.5 times more potent than novocaine.

In another series of tests on rabbits of both sexes according to the Renier method, the degree of anaesthesia of the rabbit eye cornea was determined by dripping into the conjunctival cul-de-sac of the animals 2 drops of 18.0 to 732.0 mmoles/1 of an aqueous solution of the high-molecular weight derivative of the hydrochloride of the 2-diethylaminoethyl ester of p-benzoic acid and an aqueous solution of novocaine. Each concentration was tested on 5 eyes, then the mean value of the Renier index was determined with its confidence limits at $P = 0.05$. The results indicate that the minimum concentrations of the proposed preparation sufficient to anaesthetize the rabbit eye cornea are 4 times as low as the required concentrations of the aqueous novocaine solution. From the duration of terminal anaesthesia on the rabbit eye cornea, the proposed preparation is 3 to 5 times as effective as novocaine.

Acute toxicity studies were conducted on 102 white mice of both sexes by intraperitoneal administration of 1% solution at the rate of 120 to 300 ml of the active principle per 1 kg of weight of the animal. Each dose was administered to 6 mice. As shown by observations, the clinical picture of acute poisoning induced by the proposed preparation was not materially different from that observed in the case of aqueous novocaine solution.

Acute toxicity determination was done by the graphical method according to Litchfield and Wilcoxon on punched paper by calculating the mean values with their confidence limits at $P = 0.05$. The results indicate that the proposed high-molecular weight derivative of the hydrochloride of the 2-diethylaminoethyl ester of p-aminobenzoic acid administered to white mice intraperitoneally produces the same effect as novocaine in terms of acute toxicity.

Comparing the experimental and statistical values of $LD_{50}$ for the intraperitoneal route of administration with the $EC_{50}$ values for infiltration and terminal anaesthesia, the scope of the therapeutic effect of the proposed preparation for infiltration and terminal anaesthesia was determined. Also determined was the scope of the therapeutic effect relative to novocaine.

From the scope of the therapeutic effect, the proposed preparation is 4.0 times as effective as novocaine; and from its effectiveness for terminal anaesthesia, the proposed preparation is 1.7 times as patent as novocaine.

As has been earlier indicated, the anaesthetic of this invention is composed of an active ingredient combined with a pharmaceutical solvent or an ointment base.

An isotonic solution or distilled water is employed as the pharmaceutical solvent, in accordance with the invention.

The anaesthetic of this invention as employed for infiltration anaesthesia is a 0.4 to 1% aqueous solution of the active ingredient in distilled water or an isotonic solution. Used for conduction anaesthesia, the preparation of this invention is represented by a 1.6 to 2% solution of the active ingredient in distilled water or an isotonic solution. Used for intraosseous anaesthesia, the preparation of this invention is represented by a 3.5 to 4% solution of the active ingredient in distilled water or an isotonic solution. Used for intracutaneous anaesthesia, the preparation of this invention is represented by a 0.4 to 1% solution of the active principle in distilled water or an isotonic solution.

In accordance with the invention, the proposed anaesthetic may be employed in the form of an ointment, with carboxymethyl cellulose preferably used as the ointment base.

The ointments according to the present invention comprise 1.6 to 4 wt.% of the active ingredient.

The ointments and injection solutions of the proposed preparation are prepared in the conventional manner.

The contraindications for the use of the proposed preparation are the same as for novocaine.

What we claim is:

1. A local anaesthetic, comprising an anaesthetically effective amount of an active ingredient consisting of a polymeric derivative of the hydrochloride of the 2-diethylaminoethyl ester of p-aminobenzoic acid of the following general formula:

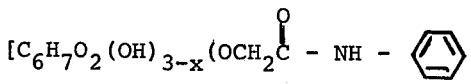

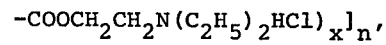

where $x$ is the degree of substitution and may range from 0.60 to 1.00 and $n$ is the degree of polymerization and may range from 40 to 120 combined with a pharmaceutical carrier selected from the group consisting of isotonic solution, distilled water and an ointment base.

2. A local anaesthetic according to claim 1, which comprises 0.40 to 1.00 wt.% of the active ingredient in isotonic solution or distilled water.

3. A local anaesthetic according to claim 1, which comprises 1.6 to 2.0 wt. % of the active ingredient in isotonic solution or distilled water.

4. A local anaesthetic according to claim 1, which comprises 3.5 to 4.0 wt. % of the active ingredient in isotonic solution or distilled water.

5. A local anaesthetic according to claim 1, which comprises carboxymethyl cellulose as the ointment base.

6. A local anaesthetic according to claim 5, which comprises 1.6 to 4.0 wt.% of the active ingredient.

* * * * *